United States Patent [19]

Lenze et al.

[11] Patent Number: 5,376,131
[45] Date of Patent: Dec. 27, 1994

[54] SUCTION SOCKET FOR ARTIFICIAL LIMB

[75] Inventors: John F. Lenze, Mineola; John Del Rossi, Northport, both of N.Y.

[73] Assignee: Manhasset Orthotics and Prosthetics, Ltd., Manhasset, N.Y.

[21] Appl. No.: 86,533

[22] Filed: Jul. 1, 1993

[51] Int. Cl.[5] ............................................. A61F 2/80
[52] U.S. Cl. ................................................ 623/34; 403/50
[58] Field of Search ...................................... 623/33-37; 602/63; 403/31, 36, 50

[56] References Cited

U.S. PATENT DOCUMENTS

| | | |
|---|---|---|
| 1,907 | 3/1865 | Parmelee . |
| 1,908 | 3/1865 | Parmelee . |
| 37,637 | 2/1863 | Parmelee . |
| 980,457 | 1/1911 | Toles . |
| 1,117,725 | 11/1914 | Tullis . |
| 1,586,015 | 1/1926 | Underwood . |
| 2,244,871 | 3/1939 | Guinzburg . |
| 2,530,285 | 12/1947 | Catranis . |
| 2,533,404 | 8/1948 | Sharp et al. . |
| 2,569,790 | 6/1950 | White et al. . |
| 2,634,424 | 4/1953 | O'Gorman . |
| 2,666,927 | 11/1952 | Morheiser . |
| 2,790,180 | 11/1955 | Hauser . |
| 2,897,512 | 8/1959 | Sackett . |
| 3,368,835 | 2/1968 | Hackforth ........................... 403/50 |
| 3,461,464 | 8/1969 | Lindgren . |
| 4,036,220 | 7/1977 | Bellasalma . |
| 4,069,600 | 1/1978 | Wise . |
| 4,564,365 | 1/1986 | Winer et al. . |
| 4,655,779 | 8/1987 | Janowiak . |
| 4,923,474 | 5/1990 | Klasson et al. . |
| 5,007,937 | 4/1991 | Fishman et al. . |

*Primary Examiner*—David H. Willse
*Attorney, Agent, or Firm*—Rosenman & Colin

[57] ABSTRACT

A stump-receiving socket for an artificial limb has an elastic diaphragm that sealingly engages a patient's stump when the stump is fully received in the socket.

11 Claims, 2 Drawing Sheets

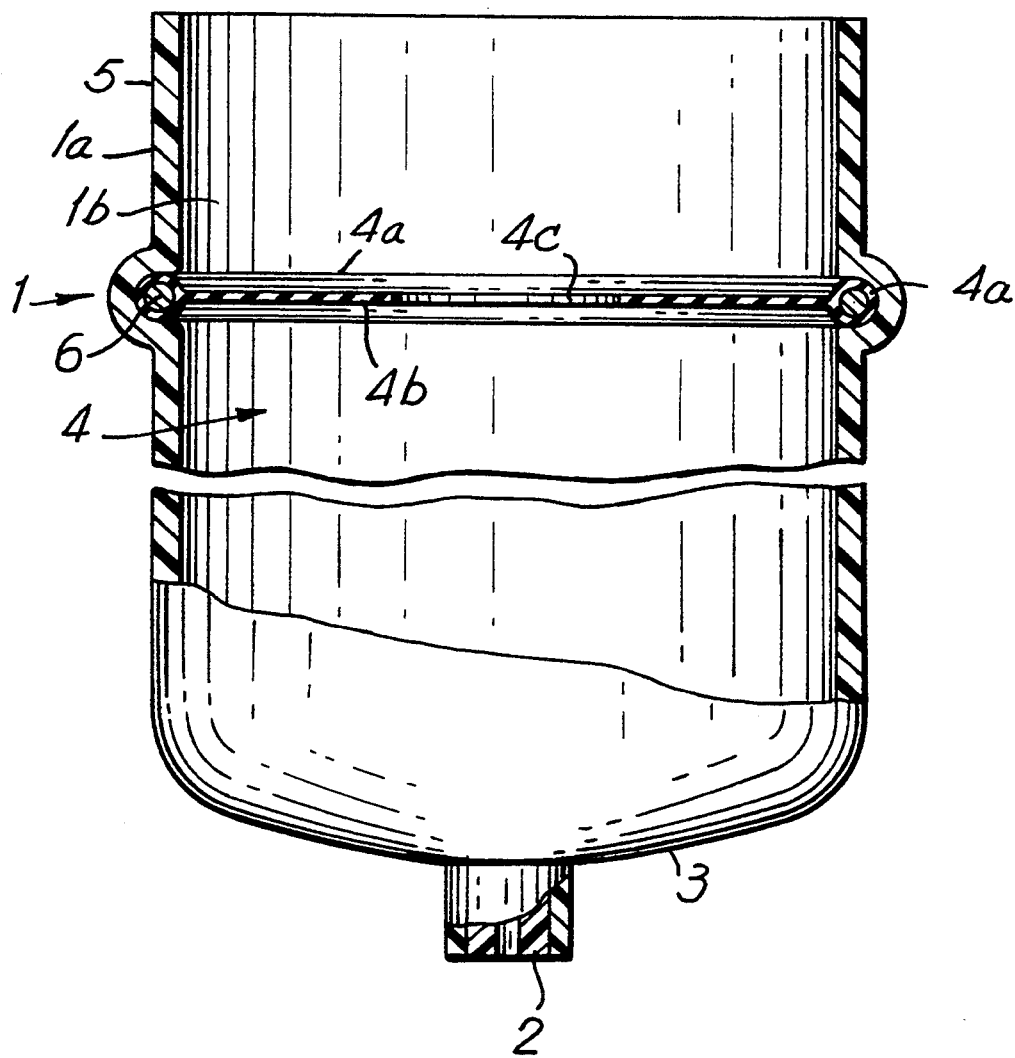
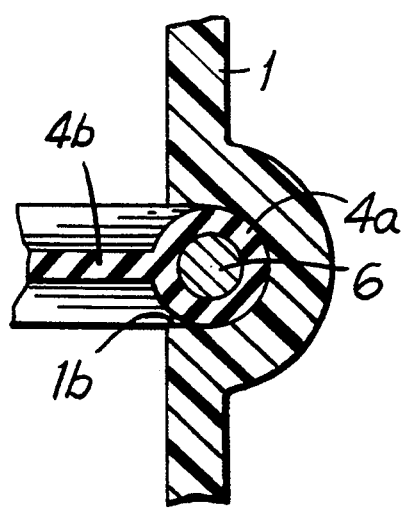
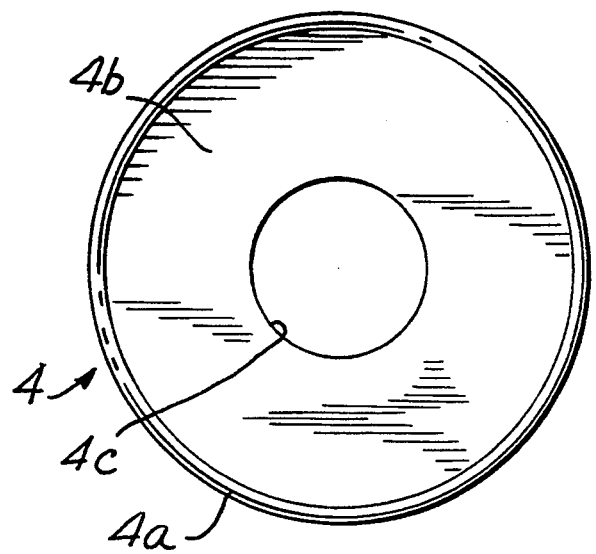

SUCTION SOCKET FOR ARTIFICIAL LIMB

The present invention relates to a prosthetic socket for use in an artificial limb, and more particularly to a suction socket of the type utilizing differential air pressure to retain a prosthetic limb on a patient's residual stump.

Artificial limbs using suction sockets are in widespread use today. These sockets are provided with a one-way air valve so that, on placing the stump of the patient's leg into the socket, the air is expelled from the interior of the socket to the outside, thus creating a partial vacuum in the airspace between the patient's stump and the interior of the socket. The difference in pressure between the atmospheric air outside the socket and the vacuum within the socket holds the socket in place until air is readmitted to the socket by opening the one-way valve.

While suction sockets have been known since the late 1800's, see, e.g., Parmelee U.S. Pat. No. 1,907, and are in widespread use today, they are not without substantial disadvantages. A major pitfall of the suction socket is the inability to provide an effective seal at the proximal open end of the socket. Even if the socket is perfectly fitted to the patient's stump, the stump will contract or shrink during the course of the day, thereby permitting air to leak into the socket, thereby reducing and in some cases completely eliminating the differential air pressure between the atmospheric air outside the socket and the airspace between the patient's stump and the socket. A variety of techniques have been adopted to address this problem, such as providing the patient with special socks to accommodate for this shrinkage. However, in practice, the patient must remove the prosthesis to apply the sock as suction is lost during the day, which is certainly inconvenient.

Another attempt to address this problem is the provision of auxiliary suspension devices, such as belts or the like, to hold the socket in place during the course of the day. This simply adds to the weight and bulk of the prosthesis and does not address the cause of the problem, namely the loss of suction due to shrinkage of the patient's stump.

The present invention provides a self-adjusting sealing member adjacent the proximal open end of the suction socket. In accordance with the present invention, the self-adjusting sealing member will maintain the seal between the proximal open end of the socket and the patient's stump as the stump shrinks during the course of the day.

In particular, the present invention provides a stump-receiving socket for an artificial limb, which comprises a tubular body member having an open proximal end and a closed distal end, a valve secured to the body member adjacent the distal end and operable to allow air to escape from the interior of the body member to the outside, and a sealing member carried by the body member adjacent to and closing the proximal open end, the sealing member comprising an elastic diaphragm extending inwardly of the body member and having a central aperture for receiving the stump of a patient's limb, the elastic diaphragm being operable to sealingly engage the stump when the stump is fully received in the body member.

In a preferred embodiment of the invention, the sealing member is removably retained in the socket, so that it can be easily removed for cleaning or replacement, if necessary.

In another preferred embodiment of the invention, the sealing member has an outer rim that is received within a correspondingly shaped groove in the interior wall of the socket. The outer rim of the sealing member comprises a flexible ring that is under compression while in the groove so that the outer rim sealingly engages the groove. The sealing member thus provides two seals, one between the elastic diaphragm and the stump and the other between the outer rim and the groove in the suction socket.

In accordance with the present invention, the elastic diaphragm of the sealing member will sealingly engage the patient's stump when it is fully received in the suction socket. As the stump shrinks during the course of the day, the elastic diaphragm will elastically contract, thereby maintaining sealing engagement between the elastic diaphragm and the patient's stump. Since the elastic diaphragm provides a perfectly sealed system, there will be no relative axial or rotational movement between the socket and the patient's stump. Moreover, there is no need for additional belts or other auxiliary suspension devices and there will be no need for the conventional socks or other inserts to take into account the shrinkage of the stump.

Moreover, whereas prior art devices depend on squeezing or compressing the residual stump to form a seal between the stump and the socket, the use of the present invention greatly reduces the pressure exerted on the leg stump, which in turn will avoid constriction of the stump with resulting impairment of circulation in the stump.

In contrast with the prior art, the present invention does not rely upon compression of the stump in the socket to maintain the socket in place, rather the elastic diaphragm uses the elasticity of the diaphragm to sealingly engage the stump. The patient will thus gain better control of the prosthesis, since the leg stump and socket are better united than the prior art. Moreover, since relative movement between the socket and stump will be eliminated or greatly reduced, the use of the suction socket of the present invention will likewise greatly decrease skin abrasions and irritations, which are at best uncomfortable and at worst can lead to serious problems.

Since the suction socket of the present invention is substantially less bulky than the prior art, due to the fact that heavy socks, inserts or suspension devices are not used, the patient will obtain psychological benefits as well as the physical benefits discussed above.

The present invention is illustrated in terms of a preferred embodiment in the accompanying drawings, in which:

FIG. 1 is a front elevational view, in section of the suction socket of the present invention;

FIG. 1A is a detail view, in section, taken along lines 1A—1A of FIG. 1, showing the sealing member sealingly engaged in the interior wall of the suction socket;

FIG. 2 is a plan view, partly in section, of the sealing member used in the present invention;

Figure 3:
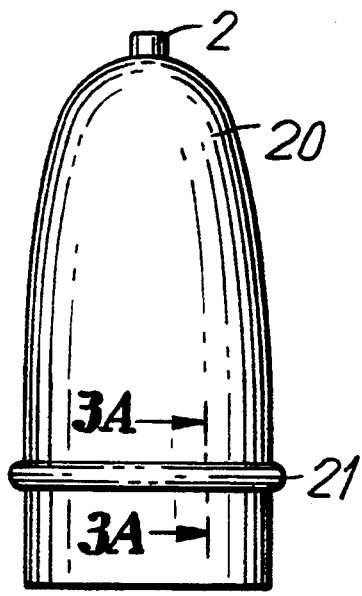
FIG. 3 is an elevational view of a casting used in the production of the suction socket of the present invention.

FIG. 1 shows a suction socket 1 comprising a tubular body member 1a having a one-way valve 2 at its closed distal end 3 and a sealing member 4 adjacent to and closing its proximal open end 5. It is presently preferred that the sealing member 4 be positioned below the proximal end 5 at a distance of about one-third the length of the socket 1. The sealing member 4 preferably lies in a plane substantially perpendicular to the longitudinal axis of tubular body member 1a. Member 4 is securely held in circumferentially extending groove 1b in socket 1. An artificial foot (not shown) is secured to the distal end 3 of socket 1.

Sealing member 4 comprises a cable 6 formed into a spring-like ring. An elastic material surrounds the cable 6 to thus form the outer rim 4a of sealing member 4. Extending from rim 4a is an elastic diaphragm or membrane or web 4b having a central aperture 4c for receiving the stump of a leg, as will be described hereinafter. It is presently preferred that cable 6 be made of metal, most preferably of stainless steel, but any bioacceptable, flexible material can be used.

The socket 1 is preferably made of a thermoplastic, bioacceptable plastic, such as those presently used in suction socket prostheses. Suitable plastics include polyolefins, such as polyethylene, polypropylene, SURLYN olefin copolymer, and the like.

One-way valve 2 may be any one-way valve, such as those used in suction sockets. Valve 2 has a spring-loaded movable valve member (not shown) that is normally spring-biased to allow air to pass only from the interior of socket 1 to the outside. However, valve 2 may be operated, in a known manner, to move the valve member against the bias of the spring to allow air to pass from the outside into the interior of socket 1. One-way valves are well known in the art and are commercially available.

Figure 3A:
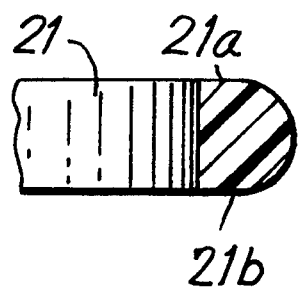
FIG. 3a is a detail view, partly in section, taken along lines 3A—3A of FIG. 3, of a template used to form a groove in the suction socket of the present invention.

The socket 1 of the invention may be produced as follows. A "positive" casting 20 (FIG. 3) of the patient's residual leg stump is prepared in the conventional manner. A flexible plastic or rubber ring 21 is fitted over the casting 20 at about one-third of the length of the casting 20. Ring 21 preferably has a flattened top 21a and bottom 21b (FIG. 3A) so that the groove 1b in socket 1 (FIG. 1A) will be similarly shaped and thus readily receive the outer rim 4a of sealing member 4. The one-way valve 2 is removably secured to the distal end of casting 20. Thereafter, the plastic socket 1 is formed by conventional vacuum-molding techniques using the casting 20 as the "model". As is known, the plastic material used for socket 1, when it is vacuum molded over the casting 20, will lock the valve 2 in place; it will not adhere to the ring 21 or the casting 20. After the socket 1 is formed, socket 1 and valve 2 are removed from the casting 20, and the ring 21 is then removed from the groove 1b. Thereafter, the ring 6 is squeezed to fold the sealing member 4, and the member 4 will elastically return to its normal shape (FIG. 2) when it is snapped into groove 1b.

In a presently preferred embodiment of the invention, the outer diameter of the sealing member 4, as measured across the rim 4a, is slightly larger than the inner diameter of socket 1 as measured across the groove 1b, so that the ring 6 is under slight compression as the sealing member is seated in groove 1b, whereby the sealing member 4 is tightly seated and securely held within the groove 1b without the need for an adhesive to keep it in place. In this manner, the sealing member can be removed for cleaning or replacement, if desired. For example, with a sealing member having a 4 inch OD elastic diaphragm 4b and a ring 6 of 0.120 inch OD, the groove 1b is suitably about 0.030 inches smaller than the outer diameter of member 4.

While any biocompatible elastic material can be used to enclose the rim 4a and provide diaphragm 4b, such as natural rubber or synthetic rubber, it is presently preferred to use a hypoallergenic elastomer, such as a silicone elastomer. Moreover, the elastomer must have sufficient toughness (hardness) and tear strength to withstand numerous cycles of use and to enable the sealing member 4 to be repeatedly removed and reinserted. Presently, it is preferred that the silicone elastomer have a durometer of more than 50, preferably more than 60.

The sealing member 4 will have a diameter suitable for the socket 1 into which the member is inserted. Preferably, the professional who will produce the leg prosthesis will have an assortment of sealing members 4 of a variety of diameters, so that a wide variety of sizes of sockets 1 can be provided with the proper size sealing member 4.

A suitable sealing member 4 may have, for example, an elastic diaphragm member 4a of about 4 inches in outer diameter, with the thickness of the elastic diaphragm being about 0.015 inches thick. A cable of about 0.12 inches in diameter is also suitable to form the ring 6. As stated above, the outer diameter of such a sealing member may be about 0.030 inch larger than the diameter of the groove 1b.

The diameter of the central aperture 4c will be empirically determined from case to case, so that there is a good seal between the leg stump and the member 4 not when the leg is fully inserted into the socket but at all times during the day. For example, a sealing member of about 4 inches in outer diameter may have a central aperture of from about 1 to about 2 inches, preferably about 1½ inches, in diameter.

Figure 4:
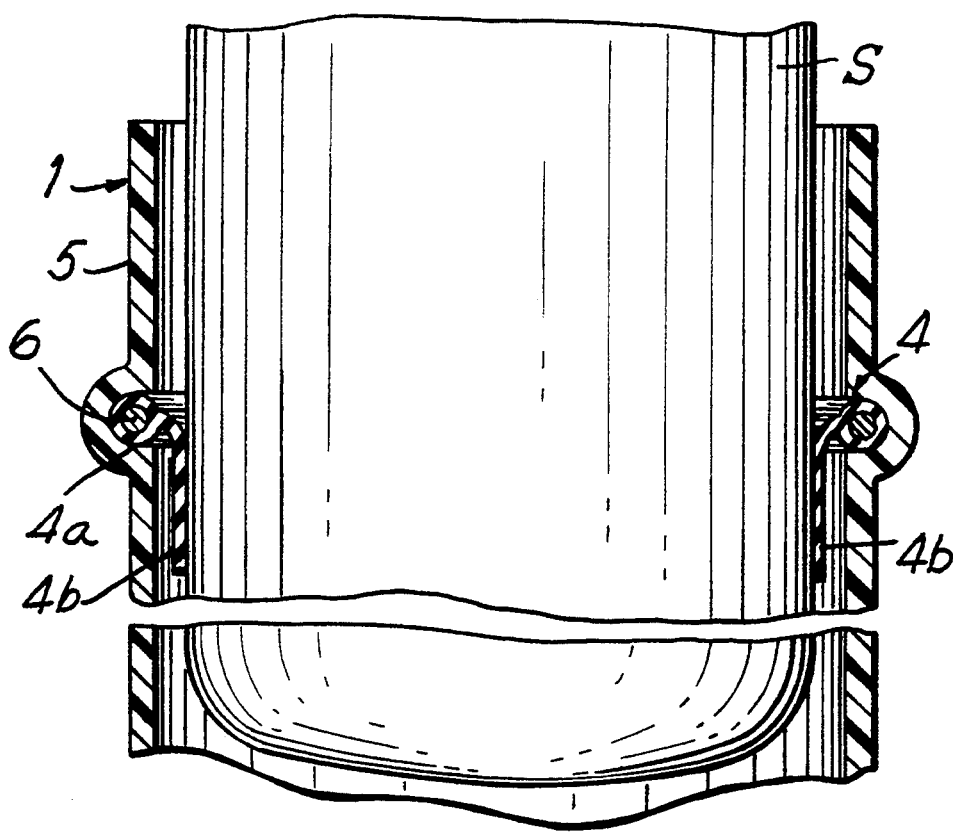
FIG. 4 is a view, similar to FIG. 1, showing the stump of a patient sealingly engaged within the suction socket of the present invention.

The socket 1 is placed over a leg stump as follows. First, a lubricant, such as a liquid skin lotion, that will not adversely react with rim 4a or diaphragm 4b is preferably applied to the stump to reduce the friction between the stump and the diaphragm 4b when donning and removing the prosthesis. The patient then inserts the leg stump downwardly into the socket 1 and slowly presses down so that the stump passes through the opening 4c in diaphragm 4b. The diaphragm 4b will elastically stretch to widen the opening 4c and will tightly and sealingly engage the stump as the stump is moved downwardly. The patient continues to push into the socket 1, causing the trapped air in the socket 1 to be expelled through valve 2. When the patient has donned the prosthesis completely (FIG. 4), the atmospheric pressure within the socket 1 is less then that outside the socket, resulting in a partial vacuum, or suction suspension. The patient may, if desired, also use any of "silicone impregnated socks" currently in use today, such as disclosed in Fishman et al U.S. Pat. No. 5,007,937.

To remove the prosthesis, valve 2 is manually operated to open the valve, thus letting air into the socket 1 as the stump is withdrawn from the socket 1.

As can be seen, the present invention provides two positive seals at the proximal end 5 of socket 1. First, since member 4 is slightly larger than the groove 1b, the cable 6 will be under compression and will thus urge the elastomeric material of the rim 4a into sealing engagement with groove 1b. Furthermore, since the opening 4c is smaller than the leg stump, the elastic diaphragm 4b is urged into sealing engagement with the leg stump.

We claim:

1. A stump-receiving socket for an artificial limb, which comprises a tubular body member having an open proximal end and a closed distal end, a valve secured to said body member adjacent said distal end and operable to allow air to escape from the interior of said body member to the outside, and a sealing member carried by said body member adjacent to and closing said proximal open end, said sealing member comprising an elastic diaphragm extending inwardly of said body member and having a central aperture for receiving the stump of a patient's limb, said elastic diaphragm being operable to sealingly engage the stump when the stump is fully received in said body member.

2. The socket according to claim 1, wherein said sealing member is detachably secured to said body member.

3. The socket according to claim 1, wherein said body member has an interior wall having a groove for receiving said sealing member.

4. The socket according to claim 1, wherein said tubular body member has a circular cross-section and said sealing member is a circular sealing member.

5. The socket according to claim 4, wherein said sealing member comprises a circular outer rim and said elastic diaphragm extends inwardly of said rim.

6. The socket according to claim 5, wherein said elastic diaphragm is composed of an elastomeric material, said outer rim comprises a flexible ring, and said flexible ring is covered by the same elastomeric material as said elastic diaphragm.

7. The socket according to claim 6, wherein said elastic diaphragm is integral with said covering of said flexible ring.

8. The socket according to claim 5, wherein said body member has an interior wall having a groove for receiving said outer rim of said sealing member.

9. The socket according to claim 8, wherein said elastic diaphragm is composed of an elastomeric material, said outer rim comprises a flexible ring, and said flexible ring is covered by the same elastomeric material as said elastic diaphragm.

10. The socket according to claim 9, wherein said flexible ring is under compression while in said groove, and said elastomeric material of said outer rim sealingly engages said groove.

11. The socket according to claim 10, wherein said elastic diaphragm is integral with said covering of said flexible ring.

* * * * *